United States Patent [19]

Hong et al.

[11] Patent Number: 5,866,160
[45] Date of Patent: Feb. 2, 1999

[54] COMPOSITION OF SOFT-SHELLED TURTLE AND TORTOISE

[75] Inventors: Mengxue Hong; Shanshan Zhong, both of Hangzhou, China

[73] Assignee: Hainan Life-Nourishing Pharmacy Co., Hainan Province, China

[21] Appl. No.: 669,322

[22] PCT Filed: Jan. 4, 1995

[86] PCT No.: PCT/CN95/00001

§ 371 Date: Sep. 3, 1996

§ 102(e) Date: Sep. 3, 1996

[87] PCT Pub. No.: WO95/18625

PCT Pub. Date: Jul. 13, 1995

[30] Foreign Application Priority Data

Jan. 4, 1994 [CN] China ............................... 94100050.8

[51] Int. Cl.$^6$ ............................... A61K 9/20; A61K 9/48
[52] U.S. Cl. .................. 424/451; 424/439; 424/455; 424/464; 424/520; 426/285; 426/521; 426/524; 426/641; 426/646; 514/879
[58] Field of Search .................... 424/456, 451, 424/455, 439, 464, 489, 520; 426/285, 521, 524, 641, 646; 514/879

[56] References Cited

U.S. PATENT DOCUMENTS 4,426,398  1/1984  Kokura et al. ............................ 426/72

FOREIGN PATENT DOCUMENTS

| 1091960 | 9/1994 | China . |
| 5675078 | 6/1981 | Japan . |
| 571980 | 1/1982 | Japan . |
| 59039270 | 12/1984 | Japan . |
| 63116642 | 11/1986 | Japan . |

OTHER PUBLICATIONS

Webster's New World Dictionary, Neufeldt, et al., pp. 1412 and 1443, Jan. 1988.

Sheng Jin–rong, et al. "The Pharmacological Research of Sea Turtle Ointment". Zhong Cheng Yao Yanjiu, 1981. No. 5, p. 42.

Primary Examiner—Thurman K. Page
Assistant Examiner—James M. Spear
Attorney, Agent, or Firm—Ladas & Parry

[57] ABSTRACT

The present invention relates to a composition of soft-shelled turtles and tortoises (TT composition) and a method for the preparation of the same. It also relates to the extensive use which is beneficial to human being.

5 Claims, No Drawings

COMPOSITION OF SOFT-SHELLED TURTLE AND TORTOISE

This application is a 371 of PCT/CN95/00001 filed Jan. 4, 1995.

FIELD OF THE INVENTION

The present invention relates to a composition of soft-shelled turtle and tortoise (TT Composition) and the preparative method thereof. It also relates to the use of the composition which is beneficial to human beings.

BACKGROUND OF THE INVENTION

In modern society, the rhythm of daily life is quicker than before. People are physically injured and mentally affected owing to the heavy work and labor which causes hypoimmunity of the organism, disorders of physiological regulation systems, fatigue and a variety of diseases. Moreover, the proportion of the aged population in society is increasing. The health care and prolonging of the life of the aged has become a prominent problem. Therefore, it is urgent to find a pharmaceutical product which is beneficial to the human body and is easy to use.

In the literature of Chinese traditional medicine, soft-shelled turtle and tortoise were recorded as effective medicinal components. However, for a long time, both of them were used only by a small number of patients or as cooked food in a restaurant. They were processed mainly in boiling water with some seasonings or steamed due to limited cookery. Their effectiveness as medicaments was not fully utilized and their application scope was greatly limited. Recently oral liquor of soft-shelled turtle and capsule of tortoise as well as food containing turtle have been developed (See Japanese Patent Publication Sho59-5020). Among these products, the effective components in the oral liquor are extracted by means of enzymatic hydrolysis, but it is not possible to micro-pulverize the mineral elements and proteins in the available turtle shell which is finally littered. As for the capsule, there is no best way to avoid complete carbonification of proteins of tortoise during the processing by the process of Chinese traditional medicine. A certain amount of nourishing components is lost. Japanese Patent Publication Sho57-1980 has disclosed a method for manufacturing turtle powder by means of pulverization under the frozen condition with the aid of liquid nitrogen, and Japanese Patent Publication Sho59-5020 has disclosed a series of nourishment-enriched foods containing turtle powder as an active principle in the form of a capsule, a granule and a tablet. However, only soft-shelled turtles are involved in these products. Therefore, there is a need to develop new products which are beneficial to humans.

SUMMARY OF THE INVENTION

The object of the present invention is to develop a composition of soft-shelled turtle and tortoise without the loss of nourishing components so that the beneficial actions of turtle and tortoise to humans are fully combined to achieve better results.

After an extensive and deep study, the inventor comes to the following invention:

The whole turtle and tortoise are pulverized under the frozen condition with the aid of liquid nitrogen. A variety of dosage forms, such as capsules etc., are made of the turtle-tortoise powder according to the conventional manner and then sterilized with irradiation.

It is found that the composition of turtle and tortoise shows a good physiological activity with a broad therapeutic spectrum, such as strengthening human resistance to diseases, regulating the central system, cardiovascular system and endocrine system, anti-senility, inhibiting action on a tumor etc.

DETAILED DESCRIPTION OF THE INVENTION

The first object of the invention relates to a TT composition, comprising 5–95% turtle by weight and 95–5% tortoise by weight.

The second object of the invention relates to a method for preparing a composition of soft-shelled turtle and tortoise, characterized in that the living turtle and tortoise are separately granulated under the frozen condition (low temperature) with the aid of liquid nitrogen; the resulted granules are dehydrated by lyophilization or other dry manner; after drying, the soft-shelled turtle granule and tortoise granule are mixed and pulverized under liquid nitrogen; and further the powder is degreased according to a conventional manner or firstly the dried products are degreased; and then pulverized under liquid nitrogen; finally, the powder is sterilized with irradiation.

The third object of the invention relates to a extensive use of TT composition for enhancing the physiological functions as a strengthening agent for the human body, regulatory agent of a variety of organ functions and nourishing tonic etc.

The advantages of TT composition indicate that the whole intrinsic nourishing components are reserved without any additives and it belongs to purely a natural product. The experiments show that TT composition of the invention is rich in a variety of amino acids and trace elements which are essential to human body, the contents of which are shown as follows:

| Contents of Amino Acids (unit: %) (From analytical results) | |
|---|---|
| 1. Aspartic acid (Asp) | 4.193 |
| 2. Threonine (Thr) | 1.628 |
| 3. Serine (Ser) | 2.049 |
| 4. Glutamic acid (Glu) | 6.327 |
| 5. Proline (Pro) | 4.113 |
| 6. Glycine (Gly) | 7.157 |
| 7. Alanine (Ala) | 3.335 |
| 8. Cysteine (Cys) | / |
| 9. Valine (Val) | 1.762 |
| 10. Methionine (Met) | 0.614 |
| 11. Isoleucine (Ile) | 1.552 |
| 12. Leucine (Leu) | 3.026 |
| 13. Tyrosine (Tyr) | 1.768 |
| 14. Phenylalanine (Phe) | 1.862 |
| 15. Histidine (His) | 1.337 |
| 16. Lysine (Lys) | 2.448 |
| 17. Ammonia ($NH_3$) | / |
| 18. Arginine (Arg) | 3.806 |
| Total amount of amino acid: | 46.976 |

Note: Model of apparatus: BECKMAN System 6300 Amino Acid Analyzer.

| Contents of vitamins: | (mg/100 g) |
|---|---|
| $VB_1$ | 11.9 |
| $VB_2$ | 1.76 |
| VE | 3.2 |

| Contents of trace elements: | (microgram/g) |
|---|---|
| Fe | 188.4 |
| Mn | 9.99 |

-continued

| | |
|---|---|
| Cu | 2.81 |
| Mg | 1862.5 |
| Cr | 9.29 |
| Sr | 95.84 |
| Zn | 137.42 |
| Contents of trace elements: | (%) |
| K | 0.31 |
| Na | 0.53 |
| Ca | 15.02 |

Analytical apparatus used: Japanese SHIMADZU AA-670

Atomic Absorption Spectrophotometer

In the preparative method of TT composition, soft-shelled turtle (Zhonghua turtle) and tortoise and/or land tortoise are used. The concrete steps are as follows:

The living turtle and tortoise less than 1 kg by weight are banned for food for at least 7 days, and then are put to death after cleaning the intestines. The dead turtle and tortoise are separately frozen soaking in liquid nitrogen under $-195°$ C. (super-low temperature) so as to make them fragile and then granulated in a size of less than 1 cm; the granules are dehydrated with lyophilization under the negative pressure or with the other means for drying in order to lower the water content to less than 4%; subsequently the dried turtle and tortoise are mixed homogeneously according to the weight ratio (5–95%:95–5%), soaked with liquid nitrogen, sprayed and pulverized into a powder in a size of more than 100 mesh by using a heavy-hammer type pulverizer with 6000 rpm/min; alternatively the dried turtle and tortoise are degreased in advance, and then the above-mentioned operation of pulverization is carried out and the powder in a size of more than 100 mesh is obtained; finally the powder of turtle and tortoise is mixed homogeneously according to the weight ratio (5–95%: 95–5%) and sterilized with irradiation.

TT composition of the invention can be made in the form of oral liquor, tablet and capsule etc. according to the conventional manner in this field and can also be added into food as a nourishing tonic. The experiments have proved that TT composition of the invention is beneficial to human body, such as strengthening resistance to disease, regulating the central system, cardiovascular system and endocrine system, eliminating fatigue, anti-senility, enhancing hematopoietic function in human, strengthening chemotherapeutic effect in carcinosis patients. The biological experiments will further illustrate the beneficial effects of TT composition on human.

Materials for Experiments

The powder of TT composition of the invention is provided by Yang Sheng Tang Tonic Co. Ltd., Hainan Province, China. The powder is made up as suspension (in 0.5% sodium carboxymethylcellulose, CMC) with the concentration of 5%, 10% and 20% separately, the suspension is administered to the mice (i.g.), volume 0.6 ml/20 g; another suspension with the concentration of 7.5%, 15% and 30% separately is administered to rats by intragastric route (ig), volume 2 ml/100 g.

Diazepam tablet: 2.5 mg/tablet, Changzhou 4th Pharmaceutical Factory, Jiangsu, China. Lot NO.921029.

Sodium Pental powder: imports, packed separately by Shanghai Chemical Reagents Purchasing and Supplying Station.

Levamisole Hydrochloride tablet: 25 mg/tablet, Xin Chang Pharmaceutical Factory, Zhejiang, China. Lot NO.921110.

Dexamethasone Acetate tablet: 0.75 mg/tablet, Wuhu 3rd Pharmaceutical Factory, China. Lot NO.921005.

Cyclophosphamide (Cy) for Injection: 200 mg/vial, Shanghai 12th Pharmaceutical Factory, China. Lot NO.880405.

Phytohaemagglutinin (PHA): Guangzhou Institute of Medicinal and Pharmaceutical Industry, China. Lot NO.860718. $^3$H-Thymidine ($^3$H-TdR): $8.14 \times 10^{11}$ /mM, Shanghai Institute of Nuclear Research, Chinese Academy of Sciences, Lot NO.911217.

Water extract of Huangqi (Astragalus root): Huangqi (sold in market) is cut to pieces, boiled in water for 3 times of 1 hour each and filtered. The combined filtrate is concentrated to 100% (i.e. each mililiter contains one gram of active principle).

Testosterone propionate Injection: 25 mg/ml, Shanghai 9th Pharmaceutical Factory. Lot NO.851004.

Estradiol valerate Injection: 10 mg/ml, Shanghai 9th Pharmaceutical Factory. Lot NO. 810501.

Model XZ-4 Counter for free motions of mice: Produced by Institute of Materia Medica, Chinese Academy of Medical Sciences. Model IRIC ARB-2050CA Scintillator: Made in USA.

Model DYQ 01 Cell Collector: Podang Medical Apparatus Factory, Shaoxing, Zhejiang, China.

Experimental Animals: NIH mice, Wistar rats, supplied by Experimental Animals Center, Zhejiang Province, China. Lot NO. ZYSYDZ 910002.

Method and Results

1. Effect on Central Nervous System 1.1 Effect on spontaneous motion of mice

Method: 75 mice (male and female, weight 18–22 g) are divided into 5 groups of 15 mice each at random. The test groups are administered (ig) with TT composition in a dose of 1.5 g, 3 g, and 6 g/kg respectively, while the control group is given normal saline in equal volume. Administration is carried out once a day for 10 days.

Diazepam group is administered (ig) with 2.5 mg/kg of diazepam on the tenth day. 30 min after administration, the mice are put into the counter separately for free motion test. The frequency of free motion of the mice within 5 min is recorded. The results from different groups are treated with statistical analysis.

Result: The test groups of 3 g and 6 g/kg of TT composition of the present invention can obviously reduce, in comparison with the control group, the frequency of spontaneous motion of the mice (See Table 1).

TABLE 1

Inhibition Effect of TT Composition on the Spontaneous Motion of Mice

| Group | No. of animal (n) | Dose (g/kg) × d | Frequency of motions (5 min) |
|---|---|---|---|
| Control | 15 | equal volume of normal saline | 143.6 ± 51.1Δ |
| TT | 15 | 1.5 × 10 | 110.4 ± 39.0 |
| TT | 15 | 3.0 × 10 | 103.6 ± 19.9* |
| TT | 15 | 6.0 × 10 | 104.5 ± 36.6* |
| Diazepam | 15 | 2.5 mg × 1 | 50.1 ± 25.7*** |

ΔAverage value ± SD, all the same in the following tables.
*$P < 0.05$,
***$P < 0.001$, t test.

1.2 Effect on sleeping rate of mice induced by sodium pental

Method: 80 mice (female, weight 18–22 g) are divided into 5 groups at random. The doses of TT composition, normal saline and diazepam (ig) are the same as the above-mentioned. 30 min after administration (ig) on the tenth day, the mice of different groups are administered intraperitoneally with the threshold dose (30 mg/kg) of sodium pental and the number of sleeping mice is noted. Disappearance of righting reflex for more than one minute is defined as the index of falling asleep in comparison with the control group.

Result: The data from test groups with 3 g/kg and 6 g/kg of TT composition in comparison with normal saline control group are treated by statistics. It shows that the falling asleep rate can be obviously enhanced by the induction of sodium pental with the threshold dose (See Table 2).

TABLE 2

Strengthening Action of TT Composition on Falling Asleep Rate in Mice Induced by Sodium Pental

| Group | No. of animal (n) | Dose (g/kg) × d | Number of mice falling asleep | Rate % |
| --- | --- | --- | --- | --- |
| Control | 16 | equal volume of normal saline | 1 | 6.3 |
| TT | 16 | 1.5 × 10 | 3 | 18.8 |
| TT | 16 | 3.0 × 10 | 7 | 43.8* |
| TT | 16 | 6.0 × 10 | 9 | 56.3** |
| Diazepam | 16 | 2.5 mg × 1 | 15 | 93.8** |

*$P < 0.05$,
**$P < 0.001$, t test or $X^2$ test.

2. Effects on Immune System

2.1 Effects on immune organs of mice under age

Method: 59 mice (female, weight 10–13 g) are divided into 5 groups at random. The doses (ig) of TT composition and normal saline are the same as the above-mentioned. Huangqi group is administered (ig) with a dose of 20 g/kg once a day for 10 days. 30 min after administration on the tenth day, the mice are put to death and the body weight is taken. After dissection, the spleen and thymus gland are weighed in wet weight. The index is calculated to compare with the control group and the difference tests are significant.

Result: TT composition of the present invention can increase the weight of immune organs very notably ($P<0.05$–0.01 respectively) (See Table 3).

TABLE 3

Weight Gain of Immune Organs of Mice under Age with TT composition

| Group | No. of animal (n) | Dose (g/kg) × d | Thymus gland index (mg/kg) | Spleen index (mg/kg) |
| --- | --- | --- | --- | --- |
| Control | 12 | equal volume of saline | 42.43 ± 4.90 | 62.57 ± 5.16 |
| TT | 12 | 1.5 × 10 | 49.45 ± 7.30* | 77.69 ± 17.72* |
| TT | 11 | 3.0 × 10 | 49.64 ± 5.54** | 79.74 ± 15.18** |
| TT | 12 | 6.0 × 10 | 49.58 ± 5.21** | 83.70 ± 8.00*** |
| Huangqi | 12 | 20.0 × 10 | 49.34 ± 5.53** | 80.42 ± 8.00*** |

*$P < 0.05$,
**$P < 0.01$,
***$P < 0.001$, t test.

2.2 Effects on transformation of lymphocytes in rats

Method: 50 rats (male, weight 150–235 g) are divided into 5 groups of 10 rats each at random. The doses of TT composition, normal saline and Huangqi water extract are the same as the above. 30 min after administration (ig) on the tenth day, 0.5 ml of blood (together with heparin as anticoagulant) is taken from the tail of rats under a sterilized condition. 0.1 ml of anticoagulant blood is taken and added into a culture tube with 3 ml of 1640 cultural solution (pH 8.0, containing PHA 100 microgram/ml, penicillin and streptomycin 100 $\mu$/ml each). After mixing homogeneously, it is cultured in a 37° C. water bath for 72 hours. After 56 hours, $^3$H-TdR $3.7 \times 10^7$ Bq is mingled. The culture lasts for another 72 hours. The above-mentioned operation must be carried out under a sterilized condition. The tube is then taken out and the T-lymphocytes mingled with $^3$H-TdR are collected in a filter film by means of a cell collector, fixed by 5% trichloroacetic acid, bleached by absolute alcohol, dried for 30 min in an oven (80° C.) and cooled. It is then set in PPO-POPOP scintillator and the data of counts per minute (cpm) are recorded. A duplicate test for each sample is necessary. The average cpm value is compared with the control group by significance test.

Result: TT composition of the present invention with the doses of 3 g/kg and 6 g/kg respectively can obviously enhance the transformation capability of lymphocytes in rats (See Table 4).

TABLE 4

Strengthening Action of TT composition on Transformation of Normal Lymphocytes in Rats

| Group | No. of animal (n) | Dose (g/kg) × d | Average cpm value per 0.1 ml whole blood |
| --- | --- | --- | --- |
| Control | 10 | equal volume of normal saline | 62219 ± 17706 |
| TT | 10 | 1.5 × 10 | 89866 ± 11419** |
| TT | 10 | 3.0 × 10 | 86705 ± 16729** |
| TT | 10 | 6.0 × 10 | 82312 ± 19662* |
| Huangqi | 10 | 20.0 × 10 | 99054 ± 20873*** |

*$P < 0.05$,
**$P < 0.01$,
***$P < 0.001$, t test.

2.3 Effect on depression of transformation capability of lymphocytes in rats induced by cyclophosphamide (Cy)

Method: 60 Rats (male, weight 180–230 g) are divided into 6 groups of 10 rats each at random. The doses of TT composition of the present invention, normal saline and Huangqi water extract are the same as above. On the seventh day, 75 mg/kg of Cy (concentration 15 mg/ml, 0.5 ml/100 g body weight) are administered (ip) except for the control group. 30 min after the last administration, 0.5 ml of anticoagulant blood is taken from the caudal vein of every animal under sterile conditions to determine the transformation capability of lymphocytes in rats with the same operation as before.

Result: TT composition of the present invention (6 g/kg) can antagonize the depression of transformation capability of lymphocytesin rats induced by Cy ($P<0.01$) (See Table 5).

TABLE 5

Effect of TT Composition on Depression of Transformation Rate of Lymphocytes in Rats Induced by Cy

| Group | No. of animal (n) | Dose (g/kg) × d | cpm/0.1 ml of whole blood |
|---|---|---|---|
| Control | 10 | / | 86480 ± 29134 |
| Cy | 10 | 75 mg/kg × 1 | 4866 ± 1821ΔΔΔ |
| Huangqi + Cy | 10 | 20.0 × 10 | 11816 ± 4006*** |
| TT + Cy | 10 | 1.5 × 10 | 5033 ± 1866 |
| TT + Cy | 10 | 3.0 × 10 | 5470 ± 1586 |
| TT + Cy | 10 | 6.0 × 10 | 7568 ± 1819** |

Cy is administered (ip, 75 mg/kg × 1) on the seventh day after previous administration
ΔΔΔP < 0.001, compared with control.
**P < 0.01, compared with Cy group,
***P < 0.001, t test.

2.4 Effect on phagocytosis of normal abdominal macrophage in mice

Method: 70 mice (male, weight 18–22 g) are divided into 5 groups of 10 mice each at random. TT Composition of 1.5 g/kg, 3.0 g/kg and 6.0 g/kg respectively, 2.5 mg/kg of levamisole and normal saline for control group are administered (ig) once a day for 10 days. 30 min after the last administration 0.5 ml of 2% chick-erythrocyte is given to the mice (ip). 2 hours later, the mice are put to death and 0.9% NaCl is injected (ip). The abdomen is rubbed slightly and cut open. The abdominal fluid is taken out for smear, followed by putting the smear on the wet gauze, and then incubated at 37° C. for half an hour, and then rinsed with 0.9% NaCl, blown to dryness and stained with 4% Giemsa-Wright for 5 min. Under the oil immersion lens, the percentage of phagocytosis in 100 macrophages is calculated, i.e. the number of macrophages which phagocytize RBC/100 macrophages× 100% and also the phagocytic index is calculated, i.e. the number of phagocytized RBC/100 macrophages. Significance tests are done for the test group in comparison with the control group.

Result: TT Composition of the present invention with the doses of 1.5 g/kg, 3 g/kg and 6 g/kg respectively can enhance very obviously the percentage of phagocytosis by abdominal macrophage in mice and phagocytotic index (P<0.001) (See Table 6).

TABLE 6

Strengthening Action of TT Composition on Phagocytosis of Normal abdominal macrophage

| Group | No. of Animal(n) | Dose (g/kg) × d | phagocytosis % | Index of phagocytosis |
|---|---|---|---|---|
| Control | 12 | equal volume of normal saline | 13.71 ± 3.81 | 0.21 ± 0.07 |
| TT | 10 | 1.5 × 10 | 33.21 ± 8.82*** | 0.52 ± 0.12** |
| TT | 10 | 3.0 × 10 | 32.69 ± 7.17*** | 0.49 ± 5.12** |
| TT | 10 | 6.0 × 10 | 48.54 ± 8.97*** | 0.74 ± 0.11** |
| Huangqi | 10 | 20.0 × 10 | 86.75 ± 9.85*** | 1.76 ± 0.22** |

**P < 0.01,
***P < 0.001, compared with control group, t test.

2.5 Effect on depression of phagocytosis of abdominal macrophage in mice induced by desamethasone Method: 72 mice (male, weight 18–22 g) are divided into 6 groups of 12 mice each at random. The doses (ig) of TT composition of the present invention, levamisole and normal saline for the control group are the same as the abovementioned. On the 7th, 8th and 9th days, 15 mg/kg of desamethasone suspension is administered (ip) to the mice except the control group. 30 min after the last administration, 0.5 ml of 2% chick-erythrocyte is administered (ip) to each mouse. After 5 hours, the mice are killed. The test operation is the same as before.

Significance tests are done for desamethasone group in comparison with the control group and the test group in comparison with desamethasone.

Result: Desamethasone administered with the dose of 15 mg/kg (ig) for 3 days can induce an obvious depression of phagocytosis of abdominal macrophage in mice (P<0.001). TT composition with the doses of 1.5 g/kg, 3 g/kg and 6 g/kg respectively can significantly antagonize the depression of phagocytosis of abdominal macrophage induced by desamethasone (P<0.001) (See Table 7).

TABLE 7

Effect of TT Composition on Phagocytosis of Abdominal Macrophage induced by desamethasone

| Group | No. of animal(n) | Dose (g/kg) × d | Phagocytosis % | Index of phagocytosis |
|---|---|---|---|---|
| Control | 12 | equal volume of normal saline | 54.82 ± 4.62 | 1.19 ± 0.17 |
| DM | 12 | 1.5 mg/kg × 3 | 37.27 ± 5.84 ΔΔΔ | 0.66 ± 0.11 ΔΔΔ |
| TT + DM | 12 | 1.5 × 10 | 58.10 ± 7.40*** | 1.11 ± 0.15*** |
| TT + DM | 10 | 3.0 × 10 | 57.80 ± 5.80*** | 1.20 ± 1.14*** |
| TT + DM | 10 | 6.0 × 10 | 67.40 ± 12.50*** | 1.46 ± 0.25*** |
| Levamisole: +DM | 10 | 20.0 × 10 | 73.91 ± 6.47*** | 1.40 ± 0.15*** |

ΔΔΔ P < 0.001, compared with control.
***P < 0.001, compared with DM group.
DM (desamethasone) 15 mg/kg × 3 days (ig).

3. Effect on Hematopoietic System

3.1 Effect on toxicity of hematopoietic system in rats caused by Cy

Method: 60 rats (male, weight 180–230 g) are divided into 6 groups of 10 rats each at random. TT composition of the present invention (1.5 g/kg, 3 g/kg and 6 g/kg respectively), 20 g/kg of Huangqi water extract Cy group and the equal volume of normal saline for control group are administered (ig) to rats once a day for 10 days. On the seventh day 75 mg/kg of Cy are administered separately to the animal except the control group. 30 min after administration the blood from the broken tail of rats are taken for counting the leukocytes and platelets.

Significance tests are done for Cy group in comparison with the control group and test groups in comparison with the Cy group.

Result: The numbers of leukocytes and platelets show a notable depression by administration (ip) of 75 mg/kg of Cy (in all cases, P<0.001). 6 g/kg of TT Composition of the present invention can effectively prevent rats from leukocytopenia induced by Cy (P<0.05), but it is not obvious in the case of thrombocytopenia (See Table 8).

TABLE 8

Protestive Action of, TT Composition against Toxicity in Hematopoietic System in rats induced by Cy

| Group | No. of animal(n) | Dose (g/kg) × d | Leukocytes (×10$^9$/L) | Platelets (×10$^9$/L) |
|---|---|---|---|---|
| Control | 12 | equal volume of normal saline | 14.05 ± 2.55 | 890 ± 182 |
| CY | 12 | 1.5 mg/kg × 3 | 3.82 ± 1.45 ΔΔΔ | 569 ± 113 ΔΔΔ |
| TT + CY | 12 | 1.5 × 10 | 4.73 ± 1.86 | 579 ± 101 |
| TT + CY | 10 | 3.0 × 10 | 5.16 ± 1.43 | 623 ± 80.4 |
| TT + CY | 10 | 6.0 × 10 | 5.28 ± 1.30* | 635 ± 140 |
| Huangqi + CY | 10 | 20.0 × 10 | 6.09 ± 1.08* | 731 ± 161* |

ΔΔΔ P < 0.001, compared with control,
*P < 0.05, compared with Cy group,
**P < 0.01, compared with Cy group, t test.

4. Effect of TT Composition on Sexual Organ and Sexual Functions

4.1 Effect on sexual organ and sexual function

Method: 60 mice (male, weight 10–13 g) are divided into 5 groups at random. TT composition of the present invention (1.5 g/kg, 3 g/kg and 6 g/kg respectively) and normal saline for the control group are administered (ig), and then 2.5 mg/kg of testosterone propionate are injected subcutaneously once a day for 10 days. 30 min after the last administration, the mice are killed, the testicle and seminal vesicle are taken out and the wet weights of them are read. The indexes are calculated.

Significance tests are done for the test group in comparison with the control group of normal saline.

Result: TT composition of the present invention with the doses of 3 g/kg and 6 g/kg respectively can obviously increase the weight of testicle and seminal vesicle of male mice under age (See Table 9).

TABLE 9

Effect of TT Composition on Weight Gain of Sexual Organ in Male Mice Under Age

| Group | No. of animal(n) | Dose (g/kg) × d | Index of testicle (mg/10 g) | vesicle (mg/10 g) |
|---|---|---|---|---|
| Control | 12 | equal volume of normal saline | 5.70 ± 0.53 | 0.82 ± 0.37 |
| TT | 12 | 1.5 × 10 | 6.01 ± 1.14 | 0.97 ± 0.43 |
| TT | 12 | 3.0 × 10 | 6.10 ± 0.40* | 1.18 ± 0.34* |
| TT | 12 | 6.0 × 10 | 6.48 ± 0.67** | 1.23 ± 0.19* |
| Testosterone | 10 | 2.5 mg/kg × 10 | 6.79 ± 0.84*** | 1.54 ± 0.46*** |

*P < 0.05, P < 0.01, *<0.001, t test.

4.2 Effect on uterus in female mice under age

Method: 58 mice (female, weight 10–13 g) are divided into 5 groups at random. The doses and administration method of TT composition of the present invention are the same as the above-mentioned. 50 micrograms/kg of estradiol valerate are injected subcutaneously once a day for 10 days. 30 min after administration, the mice are put to death. The uterus is taken out, the wet weights of them are read and the indexes are calculated.

Significance tests are done for the test group in comparison with the control group of normal saline.

Result: TT composition of the present invention with the doses of 3 g/kg and 6 g/kg respectively can obviously increase the weight of the uterus in mice (P<0.05 and 0.01 respectively) (See Table 10).

TABLE 10

Effect of TT Composition on Uterus in female mice under age

| Group | No. of animal(n) | Dose (g/kg) × d | Index of uterus (mg/10 g) |
|---|---|---|---|
| Control | 12 | equal volume of Normal Saline | 9.52 ± 2.05 |
| TT | 12 | 1.5 × 10 | 10.73 ± 1.96 |
| TT | 11 | 3.0 × 10 | 11.36 ± 2.44* |
| TT | 12 | 6.0 × 10 | 12.40 ± 2.55** |
| Estradiol valerate | 10 | 50 ug/kg × 10 | 62.98 ± 12.29*** |

*P < 0.05, P < 0.01, *P < 0.001, t test

5. Anti-stress Action 5.1 Effect on swimming test in mice

Method: 90 mice (male, weight 17–22 g) are divided into 4 groups at random. TT composition of the present invention with the doses of 1.5 g/kg, 3 g/kg and 6 g/kg respectively and normal saline for the control group are administered once a day for 10 days. 30 min after the last administration, the mice are put into a water pool (volume:length×width×height=60×30×16 cm ; temperature: 14°±1° C.) to swim. The swimming time is recorded from the time when the mice are put into the pool until they are unable to float and the heads are completely soaked in water for more than 5 sec.

Significance tests are done for the test group in comparison with the control group of normal saline.

Result: TT composition of the present invention with the doses of 3 g/kg and 6 g/kg respectively can obviously prolong the swimming time of mice (all of P<0.05) (See Table 11).

TABLB 11

Prolongation of Swimming Time of Mice by TT Composition

| Group | No. of animal(n) | Dose(g/kg) × d | Swimming time (min) |
|---|---|---|---|
| Control | 25 | equal volume of normal saline | 6.67 ± 2.38 |
| TT | 23 | 1.5 × 10 | 8.21 ± 3.78 |
| TT | 23 | 3.0 × 10 | 8.60 ± 3.35* |
| TT | 23 | 6.0 × 10 | 9.18 ± 3.59* |

*P < 0.05, t test.

5.2 Effect on tolerance to hypoxia in mice

Method: 51 mice (male and female) are divided into 4 groups at random. TT composition with the doses of 1.5 g/kg, 3 g/kg and 6 g/kg respectively and normal saline for the control group are administered once a day for 10 days. 30 min after the last administration, the mice are put into a vacuum desiccator and the pressure is gradually reduced to 700 mm Hg, time is maintained for 2.25 min. The number of dead mice is recorded.

Significance tests are done for the test group in comparison with the control group of normal saline.

Result: TT composition of the present invention with the dose of 6 g/kg can obviously enhance the capability of tolerance to hypoxia in mice, while the effects of 1.5 g/kg and 3 g/kg are not obvious (See Table 12).

TABLE 12

Effect of TT Composition on Tolerance to Hypoxia in Mice

| Group | No. of Animal(n) | Dose (g/kg × d) | number of death | Mortality % |
|---|---|---|---|---|
| Control | 14 | equal volume of normal saline | | 93.1 |
| TT | 12 | 1.5 × 10 | 10 | 83.3 |
| TT | 12 | 3.0 × 10 | | 53.8 |
| TT | 13 | 6.0 × 10 | 3 | 25.0* |

*P < 0.05. compared with control, U test or $X^2$ Test.

5.3 Effect on heat resistance.

Method: 47 mice are divided into 4 groups at random. TT composition with the doses of 1.5 g/kg, 3 g/kg and 6 g/kg respectively and normal saline for the control group are administered (ig) once a day for 10 days. 30 min after the last administration, the mice are put into a thermostat (46°±1° C.) for 42 min. The number of dead mice is recorded and $X^2$ test is done.

Result: TT composition of the present invention can enhance the capability of heat resistance in mice obviously with a dose-response-relationship (See Table 13).

TABLE 13

Effect of TT Composition on Heat Resistance in Mice

| Group | No. of animal(n) | Dose (g/kg) × d | Number of deaths | Mortality % |
|---|---|---|---|---|
| Control | 12 | equal volume of normal saline | 12 | 100 |
| TT | 12 | 1.5 × 10 | 10 | 83.3 |
| TT | 11 | 3.0 × 10 | 6 | 54.5* |
| TT | 12 | 6.0 × 10 | 3 | 25.0*** |

*P < 0.05, ***P < 0.001, compared with control, $X^2$ Test.

6. Effect on Hypoleukemia Induced by $^{60}Co$

Method: The mice are inoculated with $S_{180}$ cell suspension. 24 hours later, the mice are divided into groups of 10 mice each. TT composition of the present invention is administered to mice with the doses of 3.0 g/kg and 6.0 g/kg respectively. After 3 days, the mice accept $^{60}Co$ irradiation. Leukocyte counting is carried out on the 4th, 8th and 12th day after irradiation separately. The results are shown in Table 14. Experiment results show that TT composition of the present invention administered to $S_{180}$ mice can antagonize hypoleukemia induced by $^{60}Co$ irradiation and the detoxification effect is very remarkable (P<0.05–0.01).

TABLE 14

Effect on Hypoleukemia of $S_{180}$ Mice Induced by $^{60}Co$

| Group (test and control) and Dosage | Leukocyte × $10^3$/mm³ (X ± SD) Days after $^{60}Co$ irradiation | | |
|---|---|---|---|
| | 4 days | 8 days | 12 days |
| $^{60}Co$ 330 rad (as control) | 2.49 ± 0.69 | 3.83 ± 0.80 | 4.16 ± 0.72 |
| TT 6.0 g/kg + $^{60}Co$ 330 rad | 3.60 ± 1.28* | 5.69 ± 1.78** | 6.29 ± 1.76** |
| TT 3.0 g/kg + $^{60}Co$ 330 rad | 3.12 ± 0.77 | 4.77 ± 1.40 | 5.40 ± 1.57* |
| $^{60}Co$ 165 rad (as control) | 4.12 ± 1.07 | 5.88 ± 0.69 | 6.03 ± 0.95 |
| TT 6.0 g/kg + $^{60}Co$ 165 rad | 7.28 ± 1.93*** | 7.43 ± 1.74* | 7.67 ± 1.68* |
| TT 3.0 g/kg + $^{60}Co$ 165 rad | 5.25 ± 0.96* | 6.34 ± 1.39 | 7.22 ± 1.73 |
| $S_{180}$ mice | 9.54 ± 0.73 | 9.60 ± 0.94 | 9.96 ± 0.72 |

Notes:
1. Number of test animals: 10 mice for each group.
2. Value of normal mice (20 mice): 9.55 ± 0.89.
3. All of the P value are compared with the single irradiation group, *P < 0.05, P < 0.01,, *P < 0.001.

A composition of soft-shelled turtle and tortoise (TT Composition) can be administered to a human being without any adverse actions, side effects or toxicity. The maximal tolerant dose of mice (ig) is >52.5 g/kg.

The present invention will be further illustrated by the following preparative example, but it does not mean that the present invention will be limited by this example.

PREPARATIVE EXAMPLE 60 kg of living turtle and 40 kg of living tortoise are banned from food, for 7 days in clear water, and then the dirt in their bodies is eliminated. The pretreated turtles and tortoises are soaked in liquid nitrogen (−195° C.) and smashed separately into granules with a size of less than 1 cm. The granules are dried with dehydration to become the crude products containing less than 4% of water. 16.4 kg of turtles and 12.5 kg of tortoise, obtained from the previous procedure are mixed homogeneously, followed by spraying liquid nitrogen and smashing. A mixture of turtle and tortoise of more than 100 mesh is obtained. The mixture is degreased by conventional method and 26.7 kg of TT composition are produced. The product, TT composition, is processed into capsules in a capsule filling machine and finally sterilized with irradiation.

We claim:

1. A composition of soft-shelled turtle and tortoise (TT composition), comprising 5–95% by weight of turtle and 95–5% by weight of tortoise.

2. A composition of soft-shelled turtle and tortoise (TT Composition) according to claim 1 in the form of a liquid, capsule or tablet.

3. A method for the preparation of composition of soft-shelled turtle and tortoise (TT composition) comprising:

(1) withholding food from soft-shelled turtle and tortoise for at least 7 days and eliminating excrement from their intestines, smashing the living turtle and tortoise separately in liquid nitrogen into granules with a size of less than 1 cm, and the dirt in their intestines is eliminated;

(2) lyophilizing the granules to contain less than 4% of water;

(3) mixing the dried granules of turtles and tortoises homogeneously, spraying them with liquid nitrogen and smashing them into granules with a size of more than 100 mesh; and (4) degreasing the mixture of turtle and tortoise powder obtained from the above steps and then sterilizing said mixture with irradiation.

4. A method for strengthening immunity of a human being, regulating the central nervous system, cardiovascular system and endocrine system of a human, treating anti-senility and enhancing the leukocyte number in carcinosis patients who are undergoing chemotherapy, which comprises administering a composition of soft-shelled turtle and tortoise as claimed in claim 1 to a person in need of such treatment.

5. A method for preparing a tonic, which comprises mixing a composition of soft-shelled turtle and tortoise according to claim 1 with food.

* * * * *